US009862665B2

(12) United States Patent
Chu et al.

(10) Patent No.: US 9,862,665 B2
(45) Date of Patent: Jan. 9, 2018

(54) POLYMERIC NANOFIBROUS COMPOSITE MEMBRANES FOR ENERGY EFFICIENT ETHANOL DEHYDRATION

(71) Applicant: The Research Foundation for the State University of New York, Albany, NY (US)

(72) Inventors: Benjamin Chu, Setauket, NY (US); Benjamin S. Hsiao, Setauket, NY (US); Devinder Mahajan, South Setauket, NY (US); Tsung-Ming Yeh, Port Jefferson Station, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 466 days.

(21) Appl. No.: 14/556,473

(22) Filed: Dec. 1, 2014

(65) Prior Publication Data

US 2015/0080616 A1 Mar. 19, 2015

Related U.S. Application Data (63) Continuation of application No. 13/713,322, filed on Dec. 13, 2012, now abandoned.
(Continued)

(51) Int. Cl.
*B01D 61/36* (2006.01)
*B01D 69/12* (2006.01)
(Continued)

(52) U.S. Cl.
CPC ............ *C07C 29/76* (2013.01); *B01D 61/362* (2013.01); *B01D 61/366* (2013.01); *B01D 69/12* (2013.01);
(Continued)

(58) Field of Classification Search
CPC ...... B01D 71/02; B01D 71/028; B01D 71/10; B01D 71/26; B01D 71/38; B01D 71/40;
(Continued)

(56) References Cited

U.S. PATENT DOCUMENTS 2,882,243 A 4/1959 Milton
5,049,167 A 9/1991 Castro et al.
(Continued)

FOREIGN PATENT DOCUMENTS

WO 2004/044281 A2 5/2004
WO 2007001405 A2 1/2007

OTHER PUBLICATIONS

Paiva et al., "Effect of Functionalized Single-wall Carbon Nanotubes on PVA Morphology and Tensile Properties", Clemson University: Center for Advanced Engineering Fibers and Films (2003), Experimental.
(Continued)

*Primary Examiner* — Joseph Drodge
(74) *Attorney, Agent, or Firm* — Carter, DeLuca, Farrell & Schmidt, LLP (57) ABSTRACT

Membranes are provided for energy efficient purification of alcohol by pervaporation. Such membranes include a nanofibrous scaffold in combination with a barrier layer. The membranes also include zeolites in the barrier layer. The membranes may, in embodiments, also include a substrate.

21 Claims, 3 Drawing Sheets

Related U.S. Application Data (60) Provisional application No. 61/576,537, filed on Dec. 16, 2011.

(51) Int. Cl.

| | | |
|---|---|---|
| *B01D 69/14* | (2006.01) | |
| *B01D 71/02* | (2006.01) | |
| *B01D 71/26* | (2006.01) | |
| *B01D 71/38* | (2006.01) | |
| *C07C 29/76* | (2006.01) | |
| *C12G 3/08* | (2006.01) | |
| *B01D 71/10* | (2006.01) | |
| *B01D 71/44* | (2006.01) | |

(52) U.S. Cl.
CPC ......... *B01D 69/148* (2013.01); *B01D 71/028* (2013.01); *B01D 71/10* (2013.01); *B01D 71/26* (2013.01); *B01D 71/44* (2013.01); *C12G 3/08* (2013.01); *B01D 71/38* (2013.01); *B01D 2323/39* (2013.01); *B01D 2325/04* (2013.01); *B01D 2325/36* (2013.01)

(58) Field of Classification Search
CPC ........ B01D 71/42; B01D 71/44; B01D 71/48; B01D 71/50; B01D 71/52; B01D 71/54; B01D 71/56; B01D 71/58; B01D 71/60; B01D 61/36; B01D 61/362; B01D 61/366; B01D 69/10; B01D 69/12; B01D 69/14; B01D 69/141; B01D 69/147; B01D 69/148; B01D 2311/13; B01D 2325/04; B01D 2325/36; B01D 2325/40; B01D 71/06; B01D 71/28; C12G 3/00; C12G 3/08; C12G 3/085; C12H 1/00; C12H 1/16; C12H 1/18; C07C 29/74; C07C 29/76; C10L 2290/548
See application file for complete search history.

(56) References Cited

U.S. PATENT DOCUMENTS

| | | | |
|---|---|---|---|
| 5,230,801 A | 7/1993 | Darnell et al. | |
| 5,288,712 A | 2/1994 | Chen | |
| 5,556,539 A | 9/1996 | Mita et al. | |
| 5,968,366 A | 10/1999 | Deckman et al. | |
| 5,992,700 A * | 11/1999 | McGlothlin | A61M 5/1486 222/187 |
| 6,162,358 A | 12/2000 | Li et al. | |
| 6,472,016 B1 | 10/2002 | Soria et al. | |
| 6,500,233 B1 | 12/2002 | Miller et al. | |
| 6,536,605 B2 | 3/2003 | Rice et al. | |
| 6,582,395 B1 | 6/2003 | Burkett et al. | |
| 6,663,805 B1 | 12/2003 | Ekiner et al. | |
| 6,680,016 B2 | 1/2004 | Wang et al. | |
| 6,755,975 B2 | 6/2004 | Vane et al. | |
| 7,090,712 B2 | 8/2006 | Gillingham et al. | |
| 7,141,518 B2 | 11/2006 | MacDonald et al. | |
| 8,222,166 B2 | 7/2012 | Chu et al. | |
| 9,447,344 B2 * | 9/2016 | Kalakkunnath | C10G 45/58 |
| 2002/0014182 A1 | 2/2002 | Yadav et al. | |
| 2002/0039648 A1 * | 4/2002 | Horpel | B01D 61/362 428/307.7 |
| 2002/0173213 A1 | 11/2002 | Chu et al. | |
| 2003/0232187 A1 | 12/2003 | Kauffman et al. | |
| 2003/0233934 A1 * | 12/2003 | Wijmans | B01D 3/145 95/46 |
| 2006/0159916 A1 | 7/2006 | Dubrow et al. | |
| 2008/0110342 A1 | 5/2008 | Ensor et al. | |
| 2008/0145934 A1 | 6/2008 | Harris et al. | |
| 2008/0149561 A1 | 6/2008 | Chu et al. | |
| 2008/0237126 A1 * | 10/2008 | Hoek | B01D 67/0079 210/637 |
| 2009/0008235 A1 * | 1/2009 | Goel | B01D 3/002 203/41 |
| 2009/0057128 A1 * | 3/2009 | Vane | B01D 1/28 203/17 |
| 2009/0272692 A1 | 11/2009 | Kurth et al. | |
| 2010/0224555 A1 | 9/2010 | Hoek et al. | |
| 2013/0067803 A1 * | 3/2013 | Kalakkunnath | C10G 45/58 44/307 |

OTHER PUBLICATIONS

Paiva, et al., "Mechanical and Morphological Characterization of Polymer-Carbon Nanocomposites from Functionalized Carbon Nanotubes", Carbon 42, 2824-2854 (2004).
International Search Report from PCT Application No. PCT/US07/86549, dated Sep. 17, 2008.
International Search Report and Written Opinion from PCT Application No. PCT/US05/35738, dated Mar. 20, 2007.

* cited by examiner

POLYMERIC NANOFIBROUS COMPOSITE MEMBRANES FOR ENERGY EFFICIENT ETHANOL DEHYDRATION

CROSS REFERENCE TO RELATED APPLICATIONS

This application claims the benefit of, and priority to, U.S. patent application Ser. No. 13/713,322, filed on Dec. 13, 2012, which, in turn, claims the benefit of, and priority to, U.S. Provisional Patent Application Ser. No. 61/576,537 filed on Dec. 16, 2011, the entire disclosures of each of which are hereby incorporated by reference in their entirety.

GOVERNMENT RIGHTS

This invention was made with Government Support under grant numbers IIP0832520 and DMR1019370 awarded by the National Science Foundation. The government has certain rights in the invention.

BACKGROUND

Applications of electrospun nanofibrous membranes for liquid filtration have recently been demonstrated for microfiltration, ultrafiltration and nanofiltration. These membranes can effectively increase the permeability of a membrane formed therefrom, while maintaining high rejection ratios.

Biofuels are a wide range of fuels derived from biomass. Two of the more utilized biofuels include ethanol derived from corn grain and biodiesel derived from soybeans. There has been a steady increase in demand for biofuels, especially with the use of ethanol as an additive to gasoline in the U.S.

Industrial alcohol can be obtained from fermentation of suitable biomass (e.g. corn) using multi-staged distillation processes, which are based on the different boiling points between water, ethanol and their mixtures When ethanol is added into gasoline, its water content must be minimized because gasoline/ethanol mixture should not contain water. In other words, for most industrial and fuel applications, ethanol must be purified to minimize the water content. The final dehydration step in alcohol purification process usually requires a great deal of energy and is expensive to complete. There are also issues with exhaust/emissions. Currently, the distillation method is the most widely adopted, but it requires high energy consumption.

Membranes and methods permitting more energy efficient purification of alcohol remain desirable.

SUMMARY

The present disclosure provides pervaporation membranes (PV membranes) that include a combination of an electrospun nanofibrous scaffold and a nanocomposite hydrophilic barrier layer. Such membranes exhibit simultaneous improvements in permeation flux and separation factor, in pervaporation applications such as ethanol dehydration.

In embodiments, the present disclosure provides an article, including a pervaporation membrane, including a nanofibrous scaffold possessing fibers having a diameter of from about 1 nm to about 20,000 nm; and a hydrophilic barrier layer on at least a portion of a surface of said nanofibrous scaffold, the hydrophilic barrier layer including a polymer, wherein the nanofibrous scaffold, the hydrophilic barrier layer, or both, further include at least one zeolite.

In embodiments, an article of the present disclosure, including a pervaporation membrane, includes a substrate; a nanofibrous scaffold possessing fibers having a diameter of from about 1 nm to about 20,000 nm applied to a surface of the substrate; and a hydrophilic barrier layer on said nanofibrous scaffold on a surface opposite a surface applied to the substrate including a polymer in combination with at least one zeolite, wherein the hydrophilic barrier layer has a thickness from about 0.25 µm to about 20 µm.

Methods for producing the pervaporation membranes are also provided, as are methods for their use in purifying alcohol by pervaporation.

BRIEF DESCRIPTION OF THE FIGURES

Various embodiments of the present disclosure will be described herein with reference to the following figures, wherein.

DETAILED DESCRIPTION

As an alternative to distillation procedures, in accordance with the present disclosure, pervaporation is utilized to produce fuel grade ethanol with very low energy consumption. Pervaporation combines both permeation and evaporation to enhance the removal of water from ethanol, i.e., the dehydration of ethanol.

Pervaporation systems vary and are within the purview of those skilled in the art. Generally speaking, a pervaporation system includes, at a minimum, a supply line/feed pump, a membrane module, a withdrawal line/vacuum pump, and a condenser. Generally, a vacuum or an inert sweep gas, such as $N_2$, are applied on the permeate side of the membrane to maintain a partial pressure difference across the membrane, which facilitates volatilization of permeates for subsequent condensation and recovery.

Suitable pervaporation systems include those disclosed in U.S. Pat. Nos. 5,230,801, 5,288,712, 5,556,539, and 6,755, 975, the entire disclosures of each of which are incorporated by reference herein.

The present disclosure provides a novel pervaporation membrane (PV membrane), based on the combination of an electrospun nanofibrous scaffold and a hydrophilic barrier layer. The PV membranes of the present disclosure may be utilized with any system capable of carrying out pervaporation. In embodiments, the PV membranes of the present disclosure may be used for alcohol, such as ethanol, purification.

The membranes of the present disclosure include a composite structure with multiple layers. One layer includes a non-woven nanofibrous scaffold. In some embodiments, the scaffold layer includes electrospun nanofibers. A second layer is a barrier layer. In accordance with the present disclosure nanofibrous membranes are enhanced for pervaporation applications, such as the separation of water and ethanol.

Electrospun nanofibrous scaffolds have high porosity (up to about 80% and, in some cases, greater than about 80%), high surface to volume ratio of the material from about 4 $\mu m^{-1}$ to about 40 $\mu m^{-1}$ in embodiments from about 8 $\mu m^{-1}$ to about 20 $\mu m^{-1}$ in embodiments very high specific surface area due to fine nanofibers (having diameters from about 0.1 $\mu m$ to about 1 $\mu m$, in embodiments from about 0.2 $\mu m$ to about 0.8 $\mu m$), and interconnected-pore structures. Electrospun nanofibrous scaffolds can be used as a supporting layer in forming thin-film nanofibrous composite (TFNC) ultrafiltration and nano-filtration membranes. These membranes possess very high permeation flux from about 20 $L/m^2h$ to about 600 $L/m^2h$, in embodiments from about 100 $L/m^2h$ to about 500 $L/m^2h$ increased by a factor of from about 2 to about 10 when compared with typically commercial membranes), and a high rejection rate, in embodiments from about 80% to about 99%, in other embodiments from about 85% to about 95%.

These scaffolds may be made of suitable polymers within the purview of one skilled in the art, including, but not limited to, polyolefins including polyethylene and polypropylene, polysulfones such as polyethersulfone, fluoropolymers such as polyvinylidene fluoride, polyesters including polyethylene terephthalate, polytrimethylene terephthalate, and polybutylene terephthalate, polyamides including nylon 6, nylon 66, and nylon 12, polycarbonates, polystyrenes, polynitriles such as polyacrylonitrile, polyacrylates such as polymethyl methacrylate, polyacetates such as polyvinyl acetate, polyalcohols such as polyvinyl alcohol, polysaccharides (such as chitosan, cellulose, collagen, or gelatin), proteins such as chitin, hyaluronic acid, polyalkylene oxides such as polyethylene oxide and polyethylene glycol, polyurethanes, polyureas, polyvinyl chloride, polyimines such as polyethylene imine, polyvinylpyrrolidone, polyacrylic acids, polymethacrylic acids, polysiloxanes such as polydimethylsiloxane, poly(ester-co-glycol) copolymers, poly(ether-co-amide) copolymers, crosslinked forms thereof, derivatives thereof and copolymers thereof. In some embodiments, poly(acrylonitrile) (PAN), polyethersulfone (PES), polyvinylidenefluoride (PVDF), crosslinked water soluble polymers, e.g., polyvinylalcohol (PVA), modified cellulose and modified chitosan, their chemical derivatives and/or copolymers, may be utilized. Combinations of the foregoing may also be used to form suitable scaffolds.

In some embodiments, it may be desirable to crosslink fluid-soluble polymers to form a nanofibrous scaffold. For example, water-soluble polymers, such as polyvinyl alcohol, polysaccharides (including chitosan and hyaluronan), polyalkylene oxides (including polyethylene oxide), gelatin, and their derivatives may be crosslinked to render these polymers suitable for use as a hydrophilic nanofibrous scaffold. Crosslinking may be conducted using methods within the purview of those skilled in the art, including the use of crosslinking agents. Suitable crosslinking agents include, but are not limited to, $C_2$-$C_8$ dialdehyde, $C_2$-$C_8$ diepoxy, $C_2$-$C_8$ monoaldehydes having an acid functionality, $C_2$-$C_9$ polycarboxylic acids, combinations thereof, and the like. These compounds are capable of reacting with at least two hydroxyl groups of a water-soluble polymer.

Other suitable crosslinking methods include conventional thermal-, radiation- and photo-crosslinking reactions within the purview of those skilled in the art. Two important criteria for the selection of a crosslinking agent or method are as follows: (1) the crosslinking agent or method should not dissolve the nanofibrous scaffold layer, and (2) the crosslinking agent or method should not induce large dimensional change, e.g., hydrophilic electrospun nanofibrous scaffold layers may display very large shrinkage in hydrophobic solvents such as hydrocarbons because of their hydrophilic nature.

Specific examples of crosslinking agents which may be utilized include, but are not limited to, glutaraldehyde, 1,4-butanediol diglycidyl ether, glyoxal, formaldehyde, glyoxylic acid, oxydisuccinic acid, citric acid, fumaric acid, combinations thereof, and the like. In some embodiments, it may be useful to treat polyvinyl alcohol with a crosslinking agent such as glutaraldehyde.

The amount of crosslinking agent added to the water-soluble polymer, such as polyvinyl alcohol, may vary from about 0.1 to about 10 percent by weight of the combined weight of the crosslinking agent and polymer, in embodiments from about 0.5 to about 5 percent by weight of the combined weight of the crosslinking agent and polymer.

The thickness of the nanofibrous scaffold may vary from about 1 $\mu m$ to about 500 $\mu m$, in embodiments from about 10 $\mu m$ to about 300 $\mu m$, in embodiments from about 30 $\mu m$ to about 150 $\mu m$ in thickness. In some embodiments, the thickness of the scaffold is from about 40 $\mu m$ to about 50 $\mu m$.

The nanofibrous scaffold possesses pores or voids which assist in the functioning of the membranes of the present disclosure. The diameter of these voids may be from about 10 nm to about 200 $\mu m$, in embodiments from about 50 nm to about 30 $\mu m$, in embodiments from about 100 nm to about 10 $\mu m$. In some embodiments, the pore size may be from about 0.2 $\mu m$ to about 0.6 $\mu m$.

In forming the nanofibrous scaffold of the present disclosure, the polymer is often first placed in a solvent, such as N,N-dimethyl formamide (DMF), tetrahydrofuran (THF), methylene chloride, dioxane, ethanol, propanol, butanol, chloroform, water, or combinations of these solvents, so that the polymer is present at an amount from about 1 to about 40 percent by weight of the polymer solution, in embodiments from about 3 to about 25 percent by weight of the polymer solution, in embodiments from about 5 to about 15 percent by weight of the polymer solution.

In some embodiments, it may be desirable to add a surfactant or another solvent-miscible liquid to the polymer solution utilized to form the nanofibrous scaffold. The surfactant or other solvent-miscible liquid may lower the surface tension of the solution, which may help stabilize the polymer solution during electro-spinning, electro-blowing, and the like. Suitable surfactants include, for example, octylphenoxypolyethoxy ethanol (commercially available as TRITON X-100), sorbitan monolaurate, sorbitan sesquioleate, glycerol monostearate, polyoxyethylene, polyoxyethylene cetyl ether, dimethyl alkyl amines, methyl dialkyl amines, combinations thereof, and the like. Where utilized, the surfactant may be present in an amount from about 0.001 to about 10 percent by weight of the polymer solution, in embodiments from about 0.05 to about 5 percent by weight of the polymer solution, in embodiments from about 0.1 to about 2 percent by weight of the polymer solution. The solvent miscible fluid with the solvent forms a solvent mixture that can dissolve the polymer but changes the surface tension of the polymer solution and the evaporation rate of the solvent mixture.

In embodiments, the nanofibrous scaffold may be fabricated using electro-spinning, electro-blowing, blowing-assisted electro-spinning, and/or solution blowing technologies. Electro-spinning processes use mainly electric force, but often without the assistance of gas flow. To the contrary, solution blowing processes use only gas flow, without the use of electric force. Blowing-assisted electro-spinning and electro-blowing both use electric force and gas-blowing shear forces. In blowing-assisted electro-spinning processes, the electric force is the dominating factor, while the gas-blowing feature can assist in shearing the fluid jet stream and in controlling the evaporation of the solvent (lower throughput, smaller diameter). In contrast, in electro-blowing processes the gas-blowing force is the dominating factor to achieve the desired spin-draw ratio, while the electric force may enable further elongation of fibers (higher throughput, larger diameter).

As noted above, in embodiments, a membrane of the present disclosure includes a barrier layer applied to the nanofibrous scaffold. Suitable materials for forming the barrier layer include, in embodiments, polysaccharides such as chitosan and cellulose, polyalcohols including cross-linked PVA, polyalkylene oxides including crosslinked polyethylene oxide (PEO), their derivatives and combinations thereof. As noted above, water soluble materials such as PVA and PEO may be crosslinked with known crosslinking agents, including, but not limited to, glutaraldehyde, glyoxal, formaldehyde, glyoxylic acid, oxydisuccinic acid, citric acid, fumaric acid (FA) combinations thereof, and the like. This barrier layer, sometimes referred to as a hydrophilic barrier layer, may have a thickness from about 0.20 µm to about 20 µm, in embodiments from about 1 µm to about 10 µm, in embodiments from about 2.5 µm to about 7.5 µm.

In embodiments, either or both of the nanofibrous scaffold and barrier layers may contain zeolites. In embodiments, at least the barrier layer includes zeolites. Zeolites are solid adsorbents, sometimes referred to as molecular sieves. Zeolites are microporous crystalline solids with well-defined structures. Generally they contain silicon, aluminium and oxygen in their framework, and cations, water and/or other molecules within their pores. Many occur naturally as minerals, and are extensively mined in many parts of the world. Others are synthetic, and are made commercially for specific uses, including use as ion exchange materials, catalysts, and/or adsorbents.

As noted above, zeolites generally include a substitution of aluminum for silicon in their framework, which creates a charge imbalance that requires a non-framework cation to balance the charge. In embodiments, sodium may be included as a cation. These cations, which are contained inside the pores of these materials, may be replaced by other cations giving rise to ion-exchange properties.

Zeolites suitable for use according to the present disclosure include any known varieties, for example types A, X, P, Y, natural zeolites, and combinations thereof. The types are distinguished based upon, among other things, elements making up the zeolite, its channel/pore system, and its framework. For example, the synthesis of zeolite A is described in U.S. Pat. No. 2,882,243.

Suitable zeolites possess a significant level of crystallinity. In some embodiments, the zeolite has a mean micropore diameter from about 2.8 Angstroms to about 8 Angstroms, in embodiments from about 3 Angstroms to about 5 Angstroms, and/or an external surface area of from about 3 $m^2/g$ to about 300 $m^2/g$, in embodiments from about 100 $m^2/g$ to about 250 $m^2/g$.

Examples of suitable zeolites include those commercially available under the trade names VALFOR 100 and ADVERA 401PS, both available from PQ Corporation of Valley Forge, Pa. Also useful are zeolites in which some or all of the sodium ions have been replaced by potassium and/or calcium ions, for example zeolites 3A and 5A. Other nonlimiting examples of suitable potential ion-exchange cations include Ag, Zn, and Cu, with replacement of sodium by these cations being partial or complete.

For example, in embodiments, the hydrophilic barrier layer, in embodiments poly(vinyl alcohol), chitosan, and/or cellulose, can further contain at least one hydrophilic zeolite to enhance the pervaporation efficiency of any membrane including such a barrier layer.

In embodiments, the zeolite may be present in the hydrophilic barrier layer in amounts from about 0.1% by weight to about 50% by weight of the hydrophilic barrier layer, in embodiments from about 1% by weight to about 10% by weight of the hydrophilic barrier layer.

In embodiments, in addition to the nanofibrous scaffold and barrier layer described above, membranes of the present disclosure may also include any substrate currently in use with filtration membranes.

Such substrates include, but are not limited to, hydrophilic polymers, hydrophobic polymers, hydrophilic/hydrophobic copolymers, polyelectrolytes, and ion-containing polymers. Specific examples of polymers which may be utilized include, but are not limited to, polyolefins including polyethylene and polypropylene, polyesters including polyethylene terephthalate, polytrimethylene terephthalate and polybutylene terephthalate, polyamides including nylon 6, nylon 66, and nylon 12, polyurethanes, fluorinated polymers, polyetherketones, polystyrene, sulfonated polyetherketones, sulfonated polystyrene and derivatives thereof, cellulose and derivatives thereof, and copolymers thereof. In some embodiments, commercially available non-woven substrates made of polyethylene terephthalate (PET), propylene, including isotactic polypropylene (iPP), polyethylene (PE), glass, cellulose and cellulose-based polymers, and fluorinated polymers, may be used as the substrate.

In some embodiments, suitable substrates may include hydrophobic/hydrophilic copolymers. Such copolymers include, but are not limited to, polyurethane copolymers, polyurea copolymers, polyether-b-polyamide, PEG modified fluorinated copolymers, ethylene-propylene copolymers, cellulose based copolymers, ethylene based copolymers, propylene based copolymers, combinations thereof, and the like. These copolymers, which possess excellent mechanical strength and durability, may be useful where such characteristics are desired for the membrane.

Other suitable substrates may be porous membranes, including those fabricated by a phase inversion method. Phase inversion methods are within the purview of those skilled in the art and generally include: (1) casting a solution or mixture possessing high molecular weight polymer(s), solvent(s), and nonsolvent(s) into thin films, tubes, or hollow fibers; and (2) precipitating the polymer. The polymer may be precipitated, in embodiments, by: evaporating the solvent and nonsolvent (dry process); exposing the material to a nonsolvent vapor (e.g. water vapor), which absorbs on the exposed surface (vapor phase-induced precipitation process); quenching in a nonsolvent liquid, generally water (wet process); or thermally quenching a hot film so that the solubility of the polymer is greatly reduced (thermal process).

Suitable porous substrates, including those prepared by phase inversion processes, are within the purview of those skilled in the art and include, for example, substrates produced from polymers such as polysulfones (e.g. polyethersulfone), cellulose acetates, fluoropolymers (e.g. polyvinylidene fluoride (PVDF) and polyoxyethylene methacrylate (POEM) grafted PVDF), polyamides (e.g. poly-ether-b-polyamide), and polyimides. Such substrates may have a pore size of from about 5 nm to about 500 nm, in embodiments, from about 20 nm to about 100 nm.

In some embodiments, the substrate may be assymetrical, having varying pore sizes throughout the substrate. This asymmetry may enhance performance of a membrane utilized for pervaporation. For example, increasing porosity and/or pore diameter may enhance the mass transfer coefficient and pressure losses of a pervaporation membrane formed from such a substrate.

In some embodiments, non-woven poly(ethylene terephthalate) (PET) micro membranes (commercially available as AWA16-1 from SANKO LIMITED, 1316-1 Kawamuko cho, Tsuzuki-ku, Yokohama, 224-0044 Japan, with an average fiber diameter of about 20 μm) can be used as the substrate. In other embodiments, non-woven PET micro filters (commercially available as NOVATEXX 2413 from Freudenberg Filtration Technologies KG, D-69465 Weinheim, Germany), with an average fiber diameter of 20 μm, can be used as the substrate.

As noted above, in embodiments the substrate may be used with a nanofibrous scaffold, sometimes referred to herein as a nanofibrous membrane.

In embodiments, the scaffold layer of the membrane, such as polyacrylonitrile (PAN) or polyethersulfone (PES), may be electrospun on a substrate, such as a non-woven polyethylene terephthalate (PET) micro-filter (AWA16-1 from SANKO LIMITED, 1316-1 Kawamuko cho, Tsuzuki-ku, Yokohama, 224-0044 Japan), utilizing methods within the purview of those skilled in the art.

Where a membrane of the present disclosure possesses multiple layers, the substrate may be used to form a bottom layer having a thickness from about 1 μm to about 300 μm, in embodiments from about 10 μm to about 200 μm, in embodiments from about 50 μm to about 150 μm in thickness; the electrospun nanofibers may form a middle layer having a thickness from about 1 μm to about 100 μm, in embodiments from about 5 μm to about 75 μm, in embodiments from about 30 μm to about 50 μm in thickness; and the top hydrophilic barrier layer possessing a zeolite may have a thickness from about 0.25 μm to about 20 μm, in embodiments from about 1 μm to about 10 μm, in embodiments from about 2.5 μm to about 7.5 μm in thickness. In embodiments, these multi-layer membranes may be referred to as mixed matrix membranes ("MMM").

In embodiments, a general method for preparing membranes in accordance with the present disclosure may include the following. A PAN scaffold or ultrafiltration membrane may be e-spun in water. A casting solution, including suitable materials, such as polyvinyl alcohol, a cross-linking agent such as glutaraldehyde (GA) or fumaric acid (FA), hydrochloric acid, and/or chitosan may be prepared and cast onto the PAN scaffold. The materials may then be dried at room temperature and annealed at a suitable temperature, in embodiments about 130° C. As noted above, in embodiments, a zeolite may be added to the casting solution to form a hydrophilic barrier layer possessing a zeolite.

In some embodiments, an additional barrier layer may be placed between the middle nanofibrous layer and the top hydrophilic barrier layer. Such an additional barrier layer provides a smoother, more even surface upon which the hydrophilic barrier layer may be applied, and may prevent the intrusion/penetration of the materials utilized to form the hydrophilic barrier layer into the middle nanofibrous layer. Suitable materials for forming this additional barrier layer include, but are not limited to, cellulose nanofibers, chitin nanofibers, combinations thereof, and the like. The thickness of this additional barrier layer may be from about 0.2 μm to about 2.5 μm, in embodiments from about 0.5 μm to about 1.5 μm, in embodiments from about 0.75 μm to about 1.25 μm in thickness.

Based on the unique TFNC membrane structure, the present disclosure provides a new class of pervaporation membranes that have both a high flux and a high separation factor. In embodiments, these membranes are suitable for use in ethanol dehydration processes.

The advantages of the new class of pervaporation (PV) membranes based on nanofibrous scaffolds and nanocomposite barrier layers include the following:

(1) PV membranes having a highly porous electrospun nanofibrous scaffold as a mid-layer support can exhibit high flux.

(2) Such membranes can be used over a wide range of temperatures, from about 10 to about 100° C., which matches the operating conditions of industrial ethanol production.

(3) A wide range of hydrophilic polymers, such as cross-linked poly (vinyl alcohol), chitosan and cellulose, are available to form a dense barrier layer on the electrospun nanofibrous scaffold.

(4) The addition of hydrophilic zeolites can further increase the separation factor of the PV membranes possessing layers of highly porous electrospun nanofibrous scaffolds.

(5) The fabrication of the above PV membranes can be readily scaled up, as the mass production electrospinning process has already been demonstrated.

(6) PV membranes having a highly porous electrospun nanofibrous scaffold as a mid-layer support exhibit an excellent separation factor.

The following Examples are provided to illustrate, but not limit, the features of the present disclosure so that those skilled in the art may be better able to practice the features of the disclosure described herein.

COMPARATIVE EXAMPLE 1

A hydrophilic barrier layer of cross-linked polyvinyl alcohol (PVA) (having a thickness from about 6 to about 8 microns) was cast on a thin film nanofibrous composite, containing a very thin cellulose nanofiber additional barrier layer, an electrospun mid-layer nanofibrous scaffold (thickness about 40 microns) and a PET non-woven substrate (thickness about 120 microns). For comparison, the same cross-linked polyvinyl alcohol barrier layer was also coated on a nanofiltration membrane (a FILMTEC™ NF270 Membrane, from the Dow Chemical Company) (hereinafter "NF270") as well as on an ultrafiltration membrane made of polydimethylsiloxane (PDMS). The resulting membranes were cut into 3 inch-diameter round disc samples, which were used to evaluate the pervaporation efficiency in ethanol dehydration. In the pervaporation process, 70% ethanol was used as the feeding concentration and the operating temperature was set at 70° C.

Figure 1:
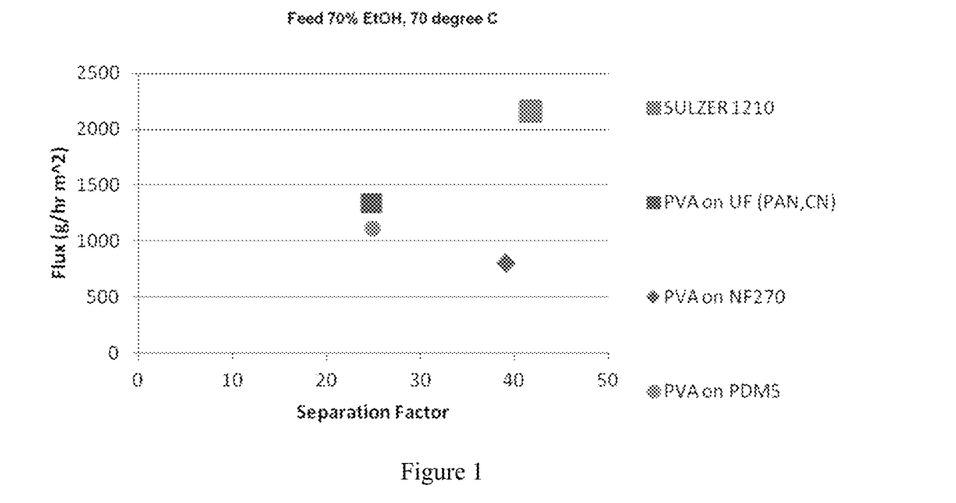
FIG. 1 is a graph comparing pervaporation performance of membranes with the same PVA barrier layer, but different scaffolds.

The pervaporation performance (i.e., flux versus separation factor) of these three membranes, as well as that of the commercial pervaporation membrane (Sulzer 1210) was calculated, with the results shown in FIG. 1.

The permeation flux was calculated using the following equation:

$$J=Q/A\Delta t \quad (I)$$

where Q=the weight of the permeate collected; A=the effective area of the membrane, and Δt=the time interval for collection.

The separation factor was calculated using the following equation:

$$\alpha = \frac{Y_W/Y_E}{X_W/X_E} \quad (II)$$

where X=the mass fraction in the feed; Y=the mass fractions in the permeate; W=water; and E=ethanol.

As seen in FIG. 1, the membrane based on the electrospun scaffold reached 1.34 (kg/m² hr) for the permeation flux, which was higher than membranes based on the two other scaffolds (PDMS and NF270). The separation factor was about the same for the electrospun scaffold and PDMS, with NF270 being the best. The barrier layer thickness of the three membranes was from about 6 to about 8 microns, several times (from about 6 to about 8 times) thicker than that of the commercial (Sulzer 1210) pervaporation membrane. Thus, the permeation flux of the membrane, normalized by the barrier layer thickness based on the electrospun scaffold, was better than that of the commercial pervaporation membrane (Sulzer 1210).

EXAMPLE 1

Additional membranes were prepared as described above in Comparative Example 1, with zeolites (zeolite 3A or zeolite 5A) added to the barrier layer. The pervaporation performance was mainly determined by the barrier layer. The incorporation of hydrophilic zeolite materials in the barrier layer (sometimes referred to herein as a nanocomposite barrier layer) significantly enhanced the separation factor, without losing the permeation flux.

Figure 2:
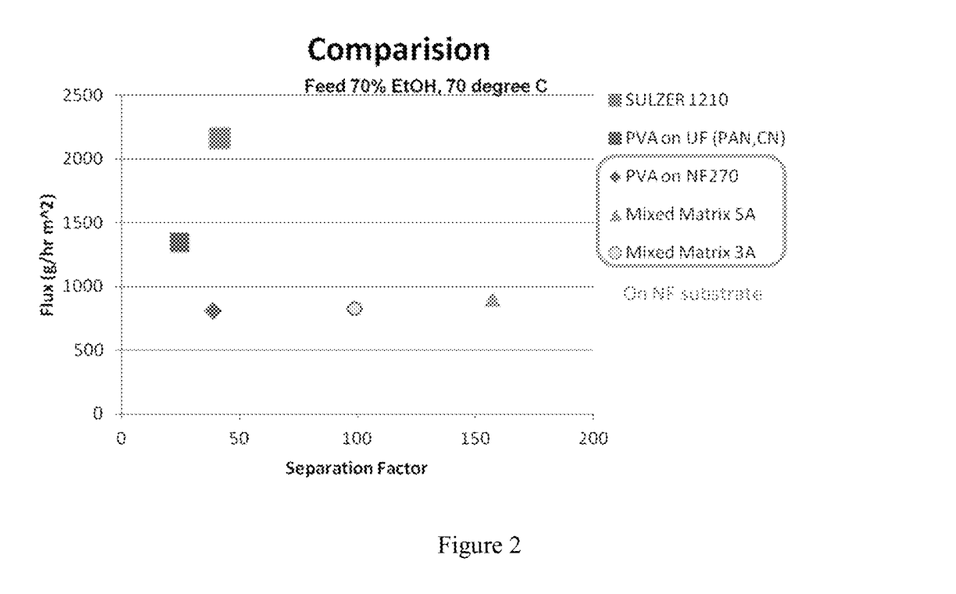
FIG. 2 is a graph comparing pervaporation performance of membranes with a nanocomposite barrier layer (containing hydrophilic zeolites) on a nanofiltration scaffold (a FILMTEC™ NF270 Membrane, from the Dow Chemical Company) (hereinafter "NF270")

The results are illustrated in FIG. 2, where the pervaporation performance of membranes based on the nanocomposite barrier layers (one contained zeolite 3A and one contained zeolite 5A) cast on a nanofibrous (NF) support, as well as that of membranes based on the unmodified barrier layer, are compared. As can be seen in FIG. 2, membranes based on the nanocomposite barrier layers (PVA and zeolite) exhibited a much higher separation factor (157.92 for zeolite 5A) than that of unmodified PVA barrier layer (39.09). The separation factor of the typical commercial pervaporation membrane (Sulzer 1210) was 47.12. The permeation flux of the three membranes containing different barrier layers but the same nanofiltration scaffold (NF 270) was about the same (0.8 kg/m² hr). Hence, the combination of the nanocomposite barrier layer (with the same thickness as the commercial pervaporation membrane) and the electrospun nanofibrous scaffold, led to simultaneous increases in permeation flux and separation factor.

To summarize the membranes of the above Example and their comparison with other membranes, a crosslinked hydrophilic poly(vinyl alcohol) barrier layer was cast on electrospun nanofibrous scaffolds of the present disclosure as well as several conventional porous membrane scaffolds (e.g. nanofiltration membrane NF270 and ultrafiltration PDMS membrane). The results indicated that the permeation flux of the membrane based on the electrospun scaffold was always higher than that obtained with conventional porous membrane scaffolds, while the separation factors were about the same among all these membranes.

Furthermore, when a hydrophilic zeolite was added to the barrier layer, the separation factor of the resulting membranes based on a conventional NF porous membrane support or nanofibrous scaffold became even higher (by 3 times) than the most successful commercial pervaporation membrane (e.g., Sulzer 1210).

Two unique features were observed for the nanofibrous membranes in pervaporation applications, such as the separation of water and ethanol. First, the membranes fabricated using the electrospun nanofibrous scaffolds had significantly higher permeation flux than those based on conventional porous membranes fabricated by a conventional phase method. Second, the barrier layer, containing hydrophilic zeolites of proper pore size and a suitable hydrophilic polymer matrix, led to substantial increase in separation factor for ethanol dehydration.

EXAMPLE 2

Additional pervaporation membranes were prepared as in Example 1 above, with modifications to the layers.

Figure 3:
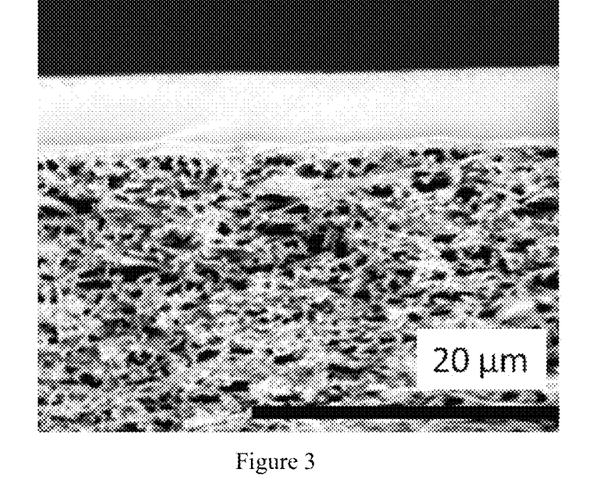
FIG. 3 is a scanning electron microscope (SEM) image of a PVA multilayered pervaporation membrane of the present disclosure. The membrane has a modified cellulose nanofibrous layer and a PVA 8 wt %/glutaraldehyde top layer.

The first modification was the use of a modified cellulose nanofibrous (CN) layer between the scaffold and barrier layer that further prevented intrusion of PVA into the fibrous scaffold. FIG. 3 is an image obtained by scanning electron microscopy (SEM) of a PVA multilayered membrane that had a modified CN layer in a lower oxidization condition. The modified CN had about 0.5 mg/mole carboxyl groups compared with an unmodified CN (having from about 1 to about 1.5 mg/mole carboxyl groups). Hence, the modified CN could form a uniform and more hydrophobic layer on the electrospun nanofibrous scaffold. By increasing the hydrophobicity of the CN layer, the casting thereon of a barrier layer including PVA (8%, cross-lined with glutaraldehyde (GA)) formed a denser layer, having a thickness of about 4 microns, which exhibited less penetration into the supporting scaffold. The modified CN layer functioned like a buffer to prevent the intrusion of the PVA into the electrospun nanofibrous scaffold during casting, thereby permitting the electrospun nanofibrous scaffold to enhance the permeant flux of the membrane.

Zeolites may be added as in Example 1 to produce membranes of the present disclosure having excellent permeation flux and separation factor.

EXAMPLE 3

Additional pervaporation membranes were prepared as in Example 2 above, with modifications to the CN layer combined with modifications to the crosslinker used in forming the PVA layer.

Figure 4:
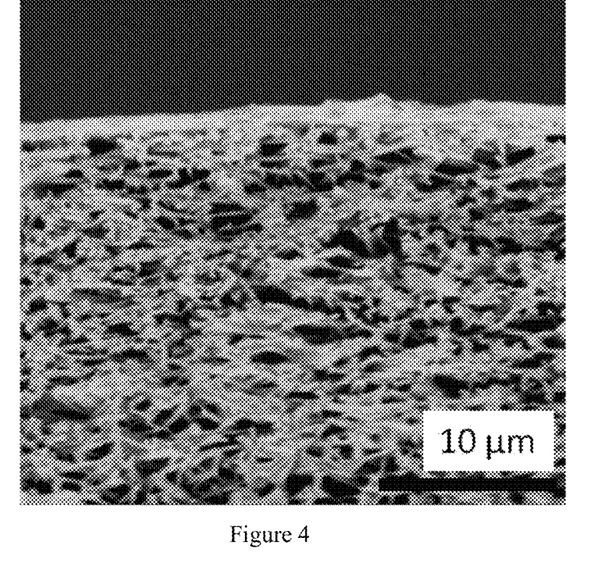
FIG. 4 is a SEM image showing a cross sectional view of a composite nanofibrous membrane of the present disclosure, possessing a modified cellulose nanofibrous layer and a PVA 2%/fumaric acid top layer.

In this example, about 0.05 molar ratio to PVA of fumaric acid (FA) (from Sigma Aldrich, USA) was used to cross-link the PVA 2 wt % used to form the barrier layer. It was found that the FA cross-linked the PVA more efficiently than PVA cross-linked by glutaraldehyde (GA), effectively reducing the thickness of the PVA barrier layer, so that the PVA barrier layer had a thickness of about 1 micron. This reduction in thickness of the PVA barrier layer, in turn, led to an increase in the permeate flux. FIG. 4 is a SEM image of a pervaporation membrane formed using the modified CN layer and fumaric acid cross-linking process (about 0.05 molar ratio to PVA, having a thickness of about 1 micron).

Additional pervaporation membranes were prepared, varying the amounts of PVA and cross-linking agent, as well as varying the cross-linking agent utilized in forming the PVA layer. Three different membranes were prepared, at varying molar ratios of cross-linking agent to PVA (with the concentration of PVA solution in weight % (wt %)) as follows:

molar ratio of GA/PVA 8 wt %=0.025;
molar ratio FA/PVA 4 wt %=0.05; and
molar ratio FA/PVA 2 wt %=0.05.

The PVA layers were cast on fibrous scaffolds possessing the modified CN layer described in Example 2, with the resulting membranes then used for ethanol dehydration. The conditions under which the pervaporation was conducted for ethanol dehydration included a feeding concentration of ethanol at about 80% by weight, at a temperature of about 70° C.

Pervaporation under the same conditions using a commercial pervaporation membrane (Sulzer 1210), was again conducted as a control.

Figure 5:
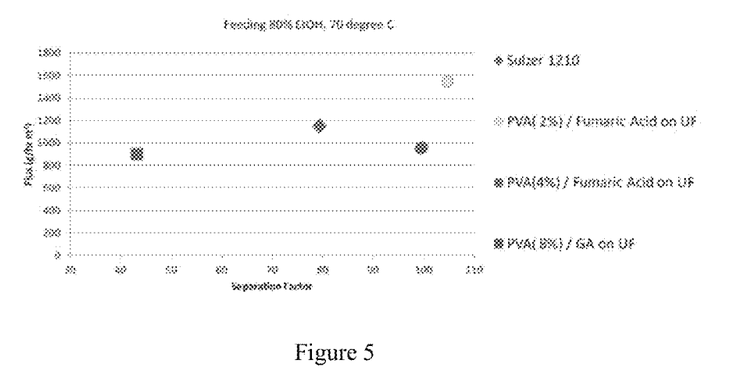
FIG. 5 is a graph comparing pervaporation performance of membranes of the present disclosure prepared with varying amounts of PVA and cross-linking agent, as well as different cross-linking agents utilized in forming the PVA layer, with a commercial pervaporation membrane.

FIG. 5 is a graph comparing the results obtained for the three pervaporation membranes and the commercial membrane. As can be seen from FIG. 5, the membrane including 0.05 molar ratio of FA/PVA 2 wt % had the best performance, with a permeate flux of 1.6 kg/m$^2$ hr, and a separation factor of 104.6. It exhibited better performance than the commercial membrane (Sulzer 1210) which had a permeate flux of 1.1 kg/m$^2$ hr, and a separation factor of 79.3.

As is apparent from the above data, the modified pervaporation membranes of this Example exhibited excellent permeant flux and very high selectivity.

Zeolites may be added as in Example 1 to produce membranes of the present disclosure having excellent permeation flux and separation factor.

While the above description contains many specific details of methods in accordance with this disclosure, these specific details should not be construed as limitations on the scope of the disclosure, but merely as exemplifications of preferred embodiments thereof. Those skilled in the art will envision many other possible variations that are all within the scope and spirit of the disclosure.

What is claimed is:

1. A method for purifying an alcohol by pervaporation, the method comprising:
   contacting an alcohol with an article comprising:
   a nanofibrous scaffold possessing at least one zeolite, the nanofibrous scaffold comprising fibers having a diameter of from about 1 nm to about 20,000 nm; and
   a hydrophilic barrier layer having a thickness from about 0.25 μm to about 20 μm on at least a portion of a surface of said nanofibrous scaffold, the hydrophilic barrier layer comprising a hydrophilic polymer selected from the group consisting of crosslinked polyvinyl alcohol, crosslinked polyethylene oxide, derivatives thereof and copolymers thereof, in combination with at least one zeolite,
   wherein the article separates water from the alcohol.

2. The method of claim 1, wherein the nanofibrous scaffold comprises a polymer selected from the group consisting of polyolefins, polysulfones, fluoropolymers, polyesters, polyamides, polycarbonates, polystyrenes, polynitriles, polyacrylates, polyacetates, polyalcohols, polysaccharides, proteins, polyalkylene oxides, polyurethanes, polyureas, polyimines, polyacrylic acids, polymethacrylic acids, polysiloxanes, poly(ester-co-glycol) copolymers, poly(ether-co-amide) copolymers, derivatives thereof, combinations thereof and copolymers thereof.

3. The method of claim 1, wherein the nanofibrous scaffold comprises a polymer selected from the group consisting of polyethylene, polypropylene, polyethersulfone, polyvinylidene fluoride, polyethylene terephthalate, polytrimethylene terephthalate, polybutylene terephthalate, nylon 6, nylon 66, nylon 12, polystyrene, polyacrylonitrile, polymethyl methacrylate, polyvinyl acetate, polyvinyl alcohol, chitosan, cellulose, collagen, gelatin, polyethylene oxide, polyethylene glycol, polyvinyl chloride, polyethylene imine, polyvinylpyrrolidone, polydimethylsiloxane, derivatives thereof, combinations thereof and copolymers thereof.

4. The method of claim 1, wherein the nanofibrous scaffold has a thickness of from about 1 μm to about 500 μm.

5. The method of claim 1, wherein the hydrophilic barrier layer has a thickness from about 0.25 to about 20 μm.

6. The method of claim 1, wherein the at least one zeolite of the nanofibrous scaffold, the hydrophilic barrier layer, or both, is selected from the group consisting of type A, type X, type P, type Y, natural zeolites, and combinations thereof.

7. The method of claim 1, wherein the at least one zeolite of the nanofibrous scaffold, the hydrophilic barrier layer, or both, has a mean micropore diameter from about 2.8 Angstroms to about 8 Angstroms.

8. The method of claim 1, wherein the at least one zeolite is present in the hydrophilic barrier layer in amounts from about 0.1% by weight to about 50% by weight of the hydrophilic barrier layer.

9. The method of claim 1, further comprising an additional barrier layer between the nanofibrous scaffold and the hydrophilic barrier layer, the additional barrier layer formed from a material selected from the group consisting of cellulose nanofibers, chitin nanofibers, and combinations thereof, wherein the additional barrier layer has a thickness from about 0.25 μm to about 2.5 μm.

10. The method of claim 1, further comprising a substrate, wherein the nanofibrous scaffold is applied to at least a portion of the substrate.

11. The method of claim 10, wherein the substrate comprises a polymer selected from the group consisting of polyolefins, polyesters, polyamides, polyurethanes, polysulfones, polyureas, fluorinated polymers, derivatives thereof, combinations thereof and copolymers thereof.

12. The method of claim 10, wherein the substrate comprises a polymer selected from the group consisting of polyethylene, polypropylene, polyethylene terephthalate, polytrimethylene terephthalate, polybutylene terephthalate, nylon 6, nylon 66, nylon 12, polyetherketones, polystyrene, sulfonated polyetherketones, sulfonated polystyrene, cellulose, derivatives thereof, combinations thereof, and copolymers thereof.

13. The method of claim 10, wherein the substrate is selected from the group consisting of polysulfones, cellulose acetates, fluoropolymers, polyamides, polyimides, and combinations thereof, and wherein the substrate has a pore size of from about 5 nm to about 500 nm.

14. The method of claim 1, wherein the pervaporation occurs at a temperature from about 10° C. to about 100° C.

15. A method for purifying an alcohol by pervaporation, the method comprising: contacting an alcohol with an article comprising:
   a substrate;

a nanofibrous scaffold comprising fibers having a diameter of from about 1 nm to about 20,000 nm in combination with at least one zeolite, a surface of the nanofibrous scaffold being applied to the substrate; and a hydrophilic barrier layer having a thickness from about 1 μm to about 10 μm on a surface of the nanofibrous scaffold opposite the surface applied to said substrate, the hydrophilic barrier layer comprising a hydrophilic polymer selected from the group consisting of crosslinked polyvinyl alcohol, crosslinked polyethylene oxide, derivatives thereof and copolymers thereof, in combination with at least one zeolite, the zeolite present in an amount from about 1% by weight to about 10% by weight of the hydrophilic barrier layer, wherein the article separates water from the alcohol.

16. The method of claim 15, wherein the substrate comprises a polymer selected from the group consisting of polyolefins, polyesters, polyamides, polyurethanes, polysulfones, polyureas, fluorinated polymers, derivatives thereof, combinations thereof and copolymers thereof.

17. The method of claim 15, wherein the nanofibrous scaffold comprises a polymer selected from the group consisting of polyolefins, polysulfones, fluoropolymers, polyesters, polyamides, polycarbonates, polystyrenes, polynitriles, polyacrylates, polyacetates, polyalcohols, polysaccharides, proteins, polyalkylene oxides, polyurethanes, polyureas, polyimines, polyacrylic acids, polymethacrylic acids, polysiloxanes, poly(ester-co-glycol) copolymers, poly(ether-co-amide) copolymers, derivatives thereof, combinations thereof and copolymers thereof.

18. The method of claim 15, wherein the nanofibrous scaffold has a thickness of from about 1 μm to about 500 μm and possesses voids with an effective diameter of from about 10 nm to about 200 μm.

19. The method of claim 15, wherein the at least one zeolite of the nanofibrous scaffold, the hydrophilic barrier layer, or both, is selected from the group consisting of type A, type X, type P, type Y, natural zeolites, and combinations thereof, having a mean micropore diameter from about 2.8 Angstroms to about 8 Angstroms.

20. The method of claim 15, wherein the at least one zeolite of the nanofibrous scaffold, the hydrophilic barrier layer, or both, is present in the hydrophilic barrier layer in amounts from about 0.1% by weight to about 50% by weight of the hydrophilic barrier layer.

21. The method of claim 15, further comprising an additional barrier layer between the nanofibrous scaffold and the hydrophilic barrier layer, the additional barrier layer formed from a material selected from the group consisting of cellulose nanofibers, chitin nanofibers, and combinations thereof, wherein the additional barrier layer has a thickness from about 0.25 μm to about 2.5 μm.

* * * * *